United States Patent [19]

Brenner et al.

[11] Patent Number: 5,627,047
[45] Date of Patent: May 6, 1997

[54] ASTROCYTE-SPECIFIC TRANSCRIPTION OF HUMAN GENES

[75] Inventors: Michael Brenner, Gaithersburg; Francois Besnard, Rockville; Yoshihiro Nakatani, Bethesda, all of Md.

[73] Assignee: United States of America Department of Health and Human Services, Washington, D.C.

[21] Appl. No.: 197,463

[22] Filed: Feb. 16, 1994

Related U.S. Application Data

[63] Continuation of Ser. No. 769,626, Oct. 4, 1991, abandoned.

[51] Int. Cl.[6] .................. C12N 15/85; C12N 15/62; C12N 15/10
[52] U.S. Cl. .................. 435/69.1; 435/69.7; 435/320.1; 435/368; 435/354; 435/325; 536/23.4; 536/23.5; 536/24.1
[58] Field of Search .................. 435/69.1, 69.7, 435/240.2, 320.1; 536/23.5, 23.4, 24.1

[56] References Cited

U.S. PATENT DOCUMENTS

| | | | |
|---|---|---|---|
| 4,736,866 | 4/1988 | Leder et al. | 800/1 |
| 5,387,742 | 2/1995 | Cordell | 800/2 |

OTHER PUBLICATIONS

Brenner, M. et al., *Mol. Brain Res.* 7 :277–286, 1990.
Nakatani, Y. et al., *J. Cell. Biochem.*, Suppl. 14B, p. 212, Abstract E556, Jan. 27–Feb. 8, 1990.
Nakahira, K. et al., *Cell Struct Funct*, 16 (6):575, Abstract 1 D–1415, 1991. (Japan, Nov. 21–23, 1991).
Nakatani, Y. et al., *Nature*, 348 :86–88, 1990 (Nov.).
Brownell, E. et al., *Genomics*, 10 : 1087–1089, 1991 (Aug.).
Bongcam-Rudloff, E. et al., *Cancer Research*, 51 :1553–1560, 1991 (March).
Reeves, S. A. et al., *PNAS*, 86 :5178–82, 1989.
Proc. Nat'l Acad. Sci. USA, vol. 87, Yoshihiro Nakatani et al.; pp. 4289–4293; Jun. 1990.
EMBO Journal; vol. 10, No. 2; Dana O. Wirak et al.; pp. 289–296; 1991.
J. of Neuroscience Research 28: (1991); "Identification of a cis–Acting Positive Regulatory Element of the Glial Fibrillary Acidic Protein Gene"; pp. 217–228.
J. of Neurochem.; (1991); "Intragenic Sequences Affect the Expression of the Gene Encoding Glial Fibrillary Acidic Protein" pp. 675–684.
Cell–Specific Expression of the Mouse Glial Fibrillary Acidic Protein Gene: Identification of the Cis–and Trans-Acting Promoter Elements for Astrocyte–Specific Expression; Masayuki Miura et al.; pp. 1180–1188.
The New Biologist; vol. 3; No. 5; May 1991; "Rapid Activation of Astrocyte–Specific Expression of GFAP–lacZ Transgene by Focal Injury"; pp. 465–474.

*Primary Examiner*—Stephen G. Walsh
*Attorney, Agent, or Firm*—Birch, Stewart, Kolasch & Birch, LLP

[57] ABSTRACT

Three unique control DNA sequences of the glial fibrillary acidic (gfa) protein gene have been identified upstream of its basal promoter that are capable of regulating astrocyte-specific transcription of the human gene for glial fibrillary acidic protein (GFAP). One or more of those three regions alone or together with the SV40 early promoter and SV40 enhancer control expression of endogenous or heterologous protein in astrocytes. Transgenic animals expressing amyloid protein can be prepared and used as a model for evaluating Alzheimer's disease. Many heterologous proteins can be expressed in the astrocytes so as to take advantage of the growing list of astrocyte functions. Such proteins include hormones, growth factors, and their receptors. Examples include basic fibroblast growth factor (bFGF), acidic FGF (aFGF), platelet derived growth factor (PDGF), insulin like growth factors 1 and 2 (IGF-1, IGF-2), epidermal growth factor (EGF), transforming growth factors $\beta$-1 and $\beta$-2 (TGF$\beta$1, TGF$\beta$2), and S100$\beta$; other examples totalled proteins encoded by oncogenes like myc, fos, and erb-a, ion channels, like the calcium channel and the potassium channel, and metabolic enzymes, especially ones involved in processing drugs or neurotransmitters; e.g., glutamine synthetase. Additionally, in each case, a dominant dysfunctional protein, an antisense RNA, or a ribozyme, all of which can inhibit the function or production of the protein, can be expressed in astrocytes.

37 Claims, 5 Drawing Sheets

Region A

-1757 aacatatcctggtgtggagtaggggacgctgctctgacagaggctcgggggcctgagc tggctctgtgagctggggaggaggcagacagccaggccttgtctgcaagcagacctgg <pre>
                       Sp I
cagcaTTGGGCTGG<u>GCCGCCCCCCAGG</u>GCctcctcttca  -1604
              <u>      hgcs       </u>
              "NF-1"
</pre>

Region B

-1612 tcctcttcatgcccagtGAAT<u>GACTCACCT</u><u>TGGCACAGACACAATGTT</u>
                          AP-1           "NF-1"

<u>CGGGGTGGGCACAGTGCCTGCT</u>tcccgccgcaccccagccccccctcaaa
      "AP-2"                      hgcs    "AP-2"

tgccttccgagaagcccattgagcagg  -1489

Region D
                          "NF-1"
-132 gagctctccccaTAG<u>CTGGGCTGCGGCCC</u><u>AACCCCACCCCCT</u>CAGgctat
                          hgcs              AP-2 gccaggggtgttgccaggggcaccc  -57

ASTROCYTE-SPECIFIC TRANSCRIPTION OF HUMAN GENES

This application is a continuation of application Ser. No. 07/769,626 filed on Oct. 4, 1991, now abandoned.

BACKGROUND OF THE INVENTION

1. Field of the Invention

The present invention relates to a gene expression system in astrocyte cells. Such a system could be used to express gene products not normally present, or to increase the expression of endogenous genes in astrocytes and transgenic animals. It could also be used to curtail gene expression as, for example, by the use of antisense RNA. Among the many uses of the present gene expression system are the evaluation of the roles of various gene products in brain development and function, and the creation of transgenic animal models possessing gliomas and afflicted with Alzheimer's disease. Such an animal model would permit the evaluation of various chemical compounds for their therapeutic effect on Alzheimer's disease. Additionally, the model could be used to test the effect of various materials and foods on that brain disease.

2. Description of Related Art

Glia make up about half the cells in the human brain. Although once thought little more than a space-filling glue, these cells are now known to participate actively in brain physiology. There are two major types of glial cells: oligodendrocytes, which ensheath nerve fibers with myelin, and astrocytes, which perform a variety of structural and metabolic functions. The list of the functions performed by astrocytes has been growing steadily, and now includes processing neurotransmitters, controlling extracellular ion levels, regulating the direction and amount of nerve growth, maintaining the blood-brain barrier, and participating in immune reactions (reviewed in 1, 2). Understanding astrocyte function is therefore central to understanding brain function. To study transcriptional controls in astrocytes, the present inventors have focused on the gfa gene, which encodes glial fibrillary acidic protein (GFAP), an intermediate filament protein found abundantly, and almost exclusively, in astrocytes (reviewed in 3). Besides serving as a convenient astrocyte-specific marker, GFAP is of interest in its own right. Synthesis of the protein is developmentally regulated, the precursors of astrocytes initially synthesizing vimentin, and then switching to GFAP near the time of birth (4). In adults, levels of GFAP increase as a result of the proliferation of astrocytes (reactive gliosis) that occurs in response to a variety of physical, chemical, and etiologic insults, including Alzheimer's disease, epilepsy, and multiple sclerosis (1, 2). GFAP is a major component of the gliotic scars which result from gliosis, and which may interfere with subsequent reinnervation.

The present inventors have previously described isolation of human cDNA and genomic clones of gfa (5), and have analyzed the structure and function of its basal promoter (6, 7). Transgenic mice have been prepared by injecting a glial fibrillary acidic protein (GFAP) hybrid construct into the germ line of mice (36). As an initial step in developing an animal model for Alzheimer's disease, a 4.5 kb DNA fragment from the 5' end of the human APP gene, which mediates neuron-specific gene expression in the CNS of transgenic mice, has been identified (37). The cloning and sequencing of the 5' flanking region of the mouse GFAP gene and the astrocyte-specific expression of a GFAP gene construct in transfected glioblastoma cells, has been reported (38). How the expression of the GFAP gene is affected by cis-acting elements in human astrocytoma and rat glioma cells has been explored (39).

It has been shown that transgenic mice whose cells contain activated oncogenic sequences are useful as a model for evaluating potential carcinogens, as well as a model for testing materials thought to confer protection against the development of neoplasma (40).

SUMMARY OF THE INVENTION

The present inventors have discovered by cell transfection experiments, sequences in the 5' flanking region of the gene that are both necessary and sufficient for its cell-specific expression. Regions of the gfa gene responsible for its astrocyte-specific expression are joined to the coding region of the gene to be expressed using standard techniques of molecular biology. The resultant chimeric DNA molecules are then introduced into cultured cells or used to make transgenic animals using standard procedures. Recombinant DNA constructs containing the chloramphenicol acetyltransferase gene are used to transfect cultured cells. An important feature of this invention is the use of the gfa regulatory sequences to restrict expression to astrocytes and astrocyte tissue. Rather than using the entire gfa gene and adjacent sequences, which extend for over 10,000 base pairs, the inventors have facilitated construction of the chimeras by identifying small subregions of the gfa gene which appear adequate to drive astrocyte-specific expression. The identified subregions are used to construct the astrocyte-specific expression system.

Accordingly, it is an object of the present invention to provide an isolated human astrocyte-specific DNA sequence capable of increasing the expression of a protein, comprising a sequence of from −2163 to +88 base pairs of the human gene for glial fibrillary acidic protein and containing three control regions upstream of its promoter, two of which regions contain the base sequence GCCGCNNCCAG (Seq. ID No. 5), with the third region having the reverse complement of said base sequence.

It is an additional object of the present invention to provide an isolated human astrocyte-specific DNA expression system comprising the DNA sequence and allelic variations thereof:

[A][B][D]

or

−2163 - - - [A][B] - - - [D] - - - +88, wherein

Region A is:

---

-1757 AACATATCCTGGTGTGGAGTAGGGGACGCTGCTCTGACAGAGGCTCGGGGGCCTGAGC
TGGCTCTGTGAGCTGGGGAGGAGGCAGACAGCCAGGCCTTGTCTGCAAGCAGACCTGG
CAGCATTGGGCTGGCCGCCCCCCAGGGCCTCCTCTTCA - 1604 (Seq. ID No. 1)

Region B is:

-1612 TCCTCTTCATGCCCAGTGAATGACTCACCTTGGCACAGACACAATGTT
CGGGGTGGGCACAGTGCCTGCTTCCCGCCGCACCCCAGCCCCCCTCAA
TGCCTTCCGAGAAGCCCATTGAGCAGG - 1489 (Seq. ID No. 2)

and Region D is:

-132 GAGCTCTCCCCATAGCTGGGCTGCGGCCCAACCCCACCCCCTCAGGCTAT
GCCAGGGGGTGTTGCCAGGGGCACCC -57 (Seq. ID No. 3)

wherein the A, B, and D regions are operably linked to a gene; and plasmids containing the isolated sequence.

It is also an object of the present invention to prepare recombinant DNA constructs and to operably link those sequences, supra, individually or together with control sequences, such as enhancers (e.g., SV40 enhancer) and promoters (e.g., gfa basal promoter) and the SV40 early promoter.

It is a further object of the present invention to prepare constructs wherein the control sequences are operably linked to endogenous as well as heterologous genes.

It is an additional object of the present invention to prepare mammalian glioma (e.g., human astrocyte) cell lines transfected with those recombinant DNA constructs.

It is another object of the present invention to prepare a transgenic non-human mammal, all of whose germ cells and nucleated somatic cells contain DNA sequences of said recombinant DNA constructs.

It is an additional object of the present invention to provide a method for increasing the expression of a protein (endogenous or heterologous), comprising transfecting a mammalian glial cell line with the recombinant DNA construct.

Further scope of the applicability of the present invention will become apparent from the detailed description and drawings provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention.

DETAILED DESCRIPTION OF THE INVENTION

The following detailed description of the invention is provided to aid those skilled in the art in practicing the present invention. Even so, the following detailed description of the invention should not be construed to unduly limit the present invention, as modifications and variations in the embodiments herein discussed may be made by those of ordinary skill in the art without departing from the spirit or scope of the present inventive discovery.

The contents of each of the references cited in the present application are herein incorporated by reference in their entirety.

Materials and Methods

General methods. All molecular biology procedures were essentially as described by Ausubel et al. (8) unless otherwise specified. Plasmid DNA was made by neutral lysis and CsCl centrifugation (9); RNA was made by the guanidinium method (8).

Plasmids. Plasmids pGEM-1, pGEM-3Z, pCAT-Promoter (pCAT-P), and pCAT-Enhancer were purchased from Promega (Madison, Wis.); pSluc2 was kindly provided by S. K. Nordeen (10); and pSVoCAT and pSV2CAT by B. H. Howard (11). pPLRCAT, which contains a polylinker inserted into the HindIII site of pSVoCAT, was obtained from M. Magnuson. It is identical to pPLFCAT (12) except the orientation of the polylinker is reversed. The pGfaCAT series of plasmids were made in this study. pGfaCAT-1 contains gfa bp −132 to +47 upstream of the CAT gene of pSVoCAT except the initiating ATG at gfa bp +15 is changed to TTG. It was made in several steps from agfa SacI fragment (−132 to +242) cloned in pGEM-1. First the plasmid was cleaved at the HindIII site adjacent to the 3' end of the insert, digested with Bal31 to gfa bp +47, cleaved at the EcoRI site adjacent to the 5' end of the insert, and cloned into the EcoRI-SmaI sites of pGEM-3Z. The ATG at gfa bp +15 was then changed to TTG by site-directed mutagenesis (13), and the resultant fragment cloned as a SacI-HindIII fragment into the SacI-HindIII sites of pPLRCAT. In the final construct, the gfa segment is thus separated at its 5' end from pSVoCAT by KpnI, BglII, and SacI sites contributed by the pPLRCAT polylinker, and at its 3' end by bp 24 to 55 of the pGEM-3Z polylinker. pGfaCAT-2 was made by inserting into the SacI site of pGfaCAT-1 the gfa SacI fragment spanning −2163 to −132. pGfaCAT-4 was derived from pGfaCAT-2 by replacing its SmaI-HindIII segment with a polymerase chain reaction (PCR)-generated fragment containing gfa sequences from −56 to +88 and carrying a HindIII site at its 3' end. Thus, pGfaCAT-4 carries gfa sequences from −2163 to +88, contains the wildtype ATG at +15, and is flanked 5' by polylinker KpnI, BglII, and SacI sites, while being joined 3' directly to the HindIII site of pSVoCA. Samples of pGfaCAT-4 were deposited under the provisions of the Budapest Treaty with the American Type Culture Collection, 12301 Parklawn Drive, Rockville, Md. 20852 USA and given the designation ATCC 75508. Except as noted below, all other pGfaCAT constructs were generated from pGfaCAT-2 (pGfaCAT-3) or pGfaCAT-4 (all others) using either convenient restriction sites (KpnI for pGfaCAT-3 and XmnI for pGfaCAT-8) or PCR-generated fragments flanked by restriction sites contributed by the amplification oligodeoxynucleotides (all others).

pGfaCAT-46, pGfaCAT-47 and pGfaCAT-65 were made from pGfaCAT-28, pGfaCAT-29 and pGfaCAT-61, respectively, by digestion with SacI and SmaI, blunt-ending with T4 DNA polymerase, and religation. pGfaCAT-22 was made by inserting a PCR-generated BglII-flanked fragment containing the SV40 enhancer (PvuII motif and two 72 bp repeats, bp 3916 to 4086 of pCAT-Enhancer) into the BglII site of pGfaCAT-1 in the forward orientation. pGfaCAT-35 was constructed by inserting a PCR-generated BglII-flanked fragment extending from gfa bp −1660 to −57 of pGfaCAT-28 into the BglII site of pCAT-P.

Cell Lines and Culture. The human glioma cell line U251 (14) was obtained from P. Kornblith; the C6 cells (rat glioma) and HepG2 cells (human hepatoblastoma) from the American Type Tissue Collection (Rockville, Md.); and the BHK (baby hamster kidney) cells from C. Chen. Primary rat astrocytes were prepared and grown in serum-containing medium as described (15). Unless otherwise noted, $1 \times 10^6$ HepG2 cells or $5 \times 10^5$ of all others were plated in 100 mm diameter dishes and maintained in Dulbecco's modified Eagle's medium (DMEM) containing 4.5 g/l glucose supplemented with 10% fetal calf serum (GIBCO, Gaithersburg, Md.). They were re-fed with fresh medium containing penicillin (50 U/ml) and streptomycin (50 ug/ml) 3 hours before transfection.

Transfection and Enzyme Assays. Except where noted, transfection was done 4 days after replating using the calcium phosphate method with 20 ug of pGfaCAT construct and 1 ug of the luciferase expression vector pSluc2. Two days after transfection, cells were harvested and luciferase assayed as described (16) using a mono-light 2010 luminometer (Analytical Luminescence Laboratory, San Diego, Calif.), except the assay buffer was 0.1M $KH_2PO_4$, pH 7.8; 5 mMATP, 12.5 mM $MgSO_4$, and 1 mM DTT. The chloramphenicol acetyltransferase (CAT) assays were performed as described (11) on the same extracts. Radioactivity on the TLC plates was then quantified with a radioanalytical vision system (AMBIS, San Diego, Calif.). CAT activities were normalized for transfection efficiency as determined by the luciferase assay, and then expressed as a percentage of the value obtained for pGfaCAT-4 in U251 cells. This activity corresponded to about 10 pmoles chloramphenicol acetylated per minute per 1,000 light units luciferase activity. A typical luciferase activity in U251 cells was 1,000 light units per ug protein. All experiments were done in duplicate and repeated at least once with comparable results.

Immunocytochemistry. Immunostaining for GFAP was done as described (17), using rabbit anti-GFAP polyclonal antibody supplied by K. Mearow.

Sequencing. DNA sequencing was performed by the Sanger dideoxy procedure using the Sequenase (modified T7 DNA polymerase) kit and instructions supplied by the United States Biochemical Corporation (Cleveland, Ohio). Both strands were sequenced, using appropriate custom oligodeoxynucleotides as primers.

DNase I Footprinting. The probe for the distal footprint was prepared from pGfaCAT-28. The plasmid was digested with BglII (in 5' polylinker), labeled using the Klenow fragment of DNA polymerase I, digested with HindIII (3' flank of insert), and the 498 bp fragment purified on an agarose gel. The 299 bp proximal probe was similarly prepared from pGfaCAT-4, using HindIII and Kpn I (−211). Nuclear extracts from U251 and HepG2 cells were prepared by the method of Dignam et al. (18), and DNase I footprinting was carried out as described by Jones et al. (19).

Northern Analysis. Samples of 10 µg RNA were fractionated on a 1.2% agarose-formaldehyde gel, blotted to nitrocellulose, and gfa RNA detected by hybridization to a probe made by random priming from the human gfa cDNA-containing EcoRI fragment of pEP163 (5).

Results

Transient transfection studies with a chloramphenicol acetyltransferase reporter gene were used to identify regions of the gfa gene responsible for its expression. Three regions, A, B, and D, were found to be important. The D region is located near the basal promoter, while A and B are next to each other about 1500 bp further upstream. The regions contain several sequences homologous to binding sites of known transcription factors, and in addition, each contains an identical novel 10 bp motif. The A, B, and D regions act in a cell-specific manner; when joined to the SV40 early promoter, they enhance transcription in the glial cell line U251, but not in the nonglial cell line HepG2. Consistent with this observation, the DNase I footprint produced in these regions by nuclear extract from U251 cells differs from that produced by an extract from HepG2 cells. The B region appears to be the most active of the three, as by itself it stimulates strong cell-specific transcription, whereas addition of the other two regions has little effect. When the B region is at its normal distance from the basal promoter, deletion of D severely reduces transcription; but when B is placed near the promoter, D is unimportant. This suggests that the D region may function primarily to promote interactions that bring B close to the promoter.

Construction of gfa-CAT reporter plasmids. To identify regions of the gfa gene that regulate its expression, we transfected cell lines with plasmids containing different 5' regions of the gfa gene inserted upstream of a chloramphenicol acetyltransferase (CAT) reporter gene. In all experiments reported here, we controlled for transfection efficiency by cotransfecting with the plasmid pSluc2, which contains the luciferase gene under the control of the SV40 early promoter (10) (see Materials and Methods for details). The first gfa plasmid yielding significant CAT activity was pGfaCAT-2, which contains gfa sequences from bp −2163 to +47, where the RNA start site is +1 (5). The region downstream of the RNA start site was included as in vitro transcription results (6) indicated that it was critical for efficient transcription. We have subsequently confirmed this observation using cell transfection (7). Since the initiating ATG is encoded in this region (bp +15, [5]), it was changed by site-directed mutagenesis (13) to TTG. To avoid the possibility that this change might affect activity of the downstream region, we also constructed a protein-fusion plasmid, pGfaCAT-4, which retains the original ATG at +15, and contains gfa sequences to +88. The activities of pGfaCAT-2 and pGfaCAT-4 were very similar (Table 1).

Cell density-dependent regulation of the gfa promoter. For our transfection studies of the human gfa gene, we chose as cell

TABLE 1

Cell specificity of pGfaCAT expression

| | CAT Activity | | | | |
|---|---|---|---|---|---|
| Plasmids | U251 | C6 | Primary Astrocytes | HepG2 | BHK |
| pSV0CAT | 30 | ND | 65 | 42 | 10 |
| pGfaCAT-1 | 10 | ND | 110 | 7 | 2 |
| pGfaCAT-2 | 77 | ND | 1007 | 2 | ND |
| pGfaCAT-4 | 100 | 1260 | ND | 2 | 2 |
| pSV2CAT | 8250 | 3750 | 3625 | 8250 | 200 |

Figure 1A:
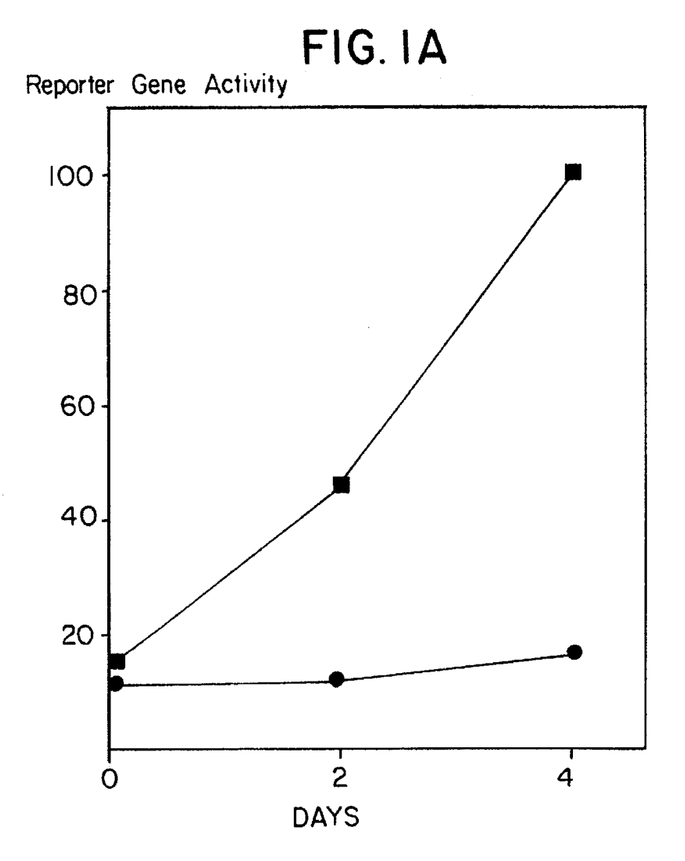
FIGS. 1A and 1B. Density-dependence of pGfaCAT-2 expression in U251 cells.
Figure 1B:
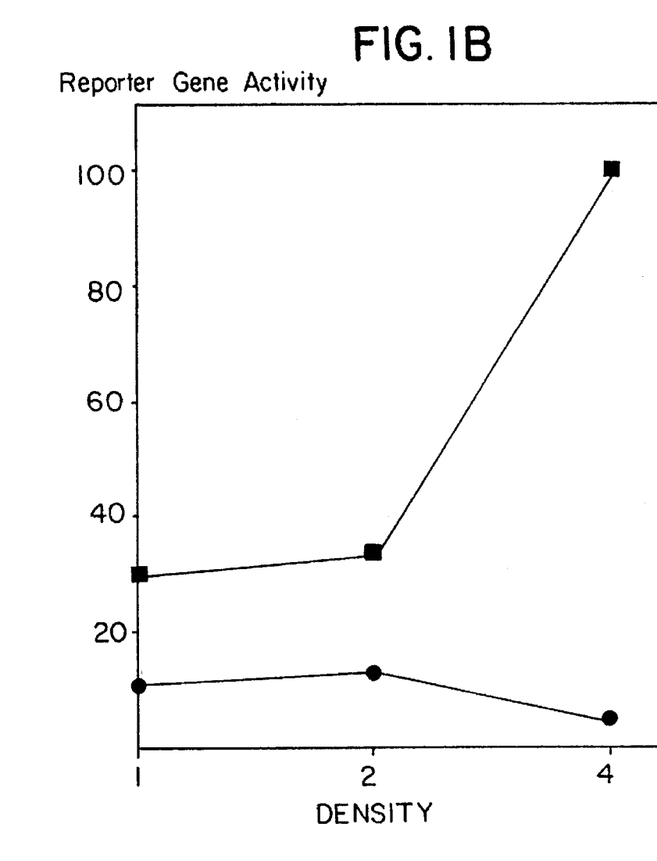

Experiments were conducted as described in Materials and Methods. pSV0CAT (negative control) is a CAT reporter gene without enhancer or promoter.
pSV2CAT (positive control) is a CAT reporter gene with the SV40 enhancer and promoter, upstream of the CAT gene. Values are expressed as the percentage of that of pGfaCAT-4 in U251 cells.
ND indicates not done.

host the strongly GFAP-positive human glioma cell line U251. Standard transfection protocols specify transfecting cells the day of replating and harvesting 1 or 2 days later. However, the quantity of GFAP protein in C6 cells has been found to be low upon replating, and then to increase substantially once the culture became confluent (20). To determine if the amount of endogenous GFAP in U251 cells is regulated similarly, and to determine if this regulation might occur at the transcriptional level, we used Northern analysis and immunocytochemistry to follow levels of gfa mRNA and GFAP, respectively. Both gene products were found to be present at low levels for several days following replating, and then to increase markedly as the culture reached confluency (data not shown). Considering it likely that expression of the transfected gfa-CAT constructs would follow a similar pattern, we determined whether CAT activity would be increased by delaying transfection for several days after plating, or by plating cells at a higher initial density. FIGS. 1A and 1B show that both these strategies were successful. Experiments were conducted as described in Materials and Methods except for variation in the interval between replating and transfection (A) or the number of cells plated (B). (A) The abscissa values are the intervals between plating and transfection. Cells grew with about a 30-hour generation time and reached confluency in 3–4 days. (B) The abscissa values are the fold-increase in plating density over the standard value. For the first time point in (A) and for all in (B), cells were transfected 3 hours after plating. All cells were harvested 2 days after transfection. ■ CAT activity normalized for transfection efficiency and expressed as a percentage of the maximum value; ● luciferase activity in 100s of light units per μg protein. For convenience, we adopted the procedure of plating at the standard density and transfecting 4 days later.

Figure 2:
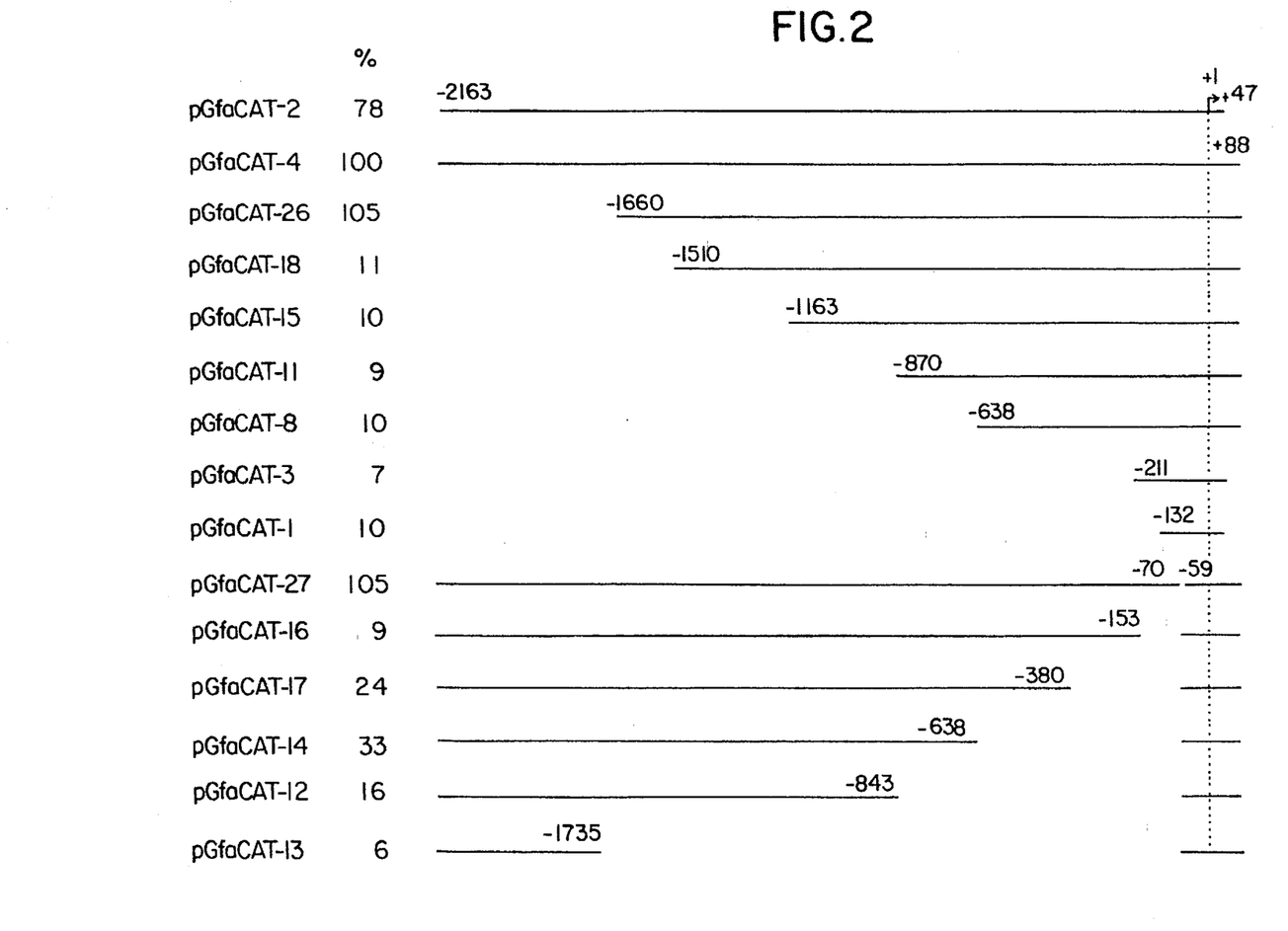
FIG. 2. Effect of 5' and 3' deletions of the gfa upstream region.

Localization of regions contributing to gfa expression. To identify the specific regions required for transcriptional activity, a series of 5' and 3' deletions of the gfa upstream region was constructed. The relative CAT activities of these constructs could be expected to reflect gfa-induced transcription, as primer extension showed that about 95% of the CAT mRNA present in cells transfected with pGfaCAT-4 is initiated from the correct gfa mRNA startpoint (7). Results obtained are shown in FIG. 2. Numbers at either end of the solid lines indicate the endpoints of the gfa regions included in the plasmids. Normalized CAT activity in U251 cells as a percent of that of pGfaCAT-4 is listed in the % column. Analysis of the 5' deletion series (FIG. 2) indicated that the region between −2163 and −1661 is dispensible, but that an important regulatory sequence is present between −1660 and −1511. Deletion of this region produced over a 5-fold reduction in CAT activity. Results from the series of 3' deletions of the upstream region (FIG. 2) indicated that a region between −152 and −70 is also required for full activity. Excision of this segment reduced CAT activity to 10% that of pGfaCAT-4. Interestingly, the activity remaining upon deletion of this region increased to 20–30% when additional sequences between it and the regulatory region further upstream were removed.

To determine if the distal upstream region and the proximal upstream region are sufficient as well as necessary for gfa-directed expression, these two regions were joined using a convenient SacI site at −132. Not only did the resultant construct (pGfaCAT-28) support CAT expression, but it did so at about ten times the level of its pGfaCAT-4 parent (Table 2, last line). With the present construct gfa directed expression can be increased by as much as 5–1,000 fold, particularly 10–100 fold. The increased activity could be due to the closer juxtaposition of the upstream region to the promoter, to removal of an intervening negative element, or to a combination of these effects.

Footprint of the regulatory regions. To localize the potential cis-acting elements required for gfa transcription, we conducted DNase I footprinting experiments using the two regulatory regions identified above. Nuclear extracts from U251 cells produced two protected regions within the distal regulatory region (FIG. 3A), one between −1636 and −1614, and the other between −1596 and −1543. Numbers on either side of the figure give positions relative to the RNA start site as determined by Maxam Gilbert A+G sequencing reactions. Vertical bars indicate footprinted regions. The proximal region (FIG. 3B) also contained two protected regions, a strong footprint between −120 and −88, and a weak one between −144 and −128. Because most of the region covered by this latter footprint was missing from the highly active pGfaCAT-28, it was not analyzed further. The footprints produced by the HepG2 extract will be discussed below.

Activator activity of specific regions. On the basis of the footprint data, we divided the distal regulatory region present in pGfaCAT-28 into two segments for further analysis; region A

TABLE 2

Effect of the gfa A,B and D regions on CAT expression in U251 and HepG2 cells

| | Upstream | | | CAT Activity | |
|---|---|---|---|---|---|
| Plasmid | Region | | | U251 | HepG2 |
| pGfaCAT-1 | | | D | 10 | 7 |
| pGfaCAT-47 | | B | | 500 | 25 |
| pGfaCAT-65 | A | | | 60 | nd |
| pGfaCAT-61 | A | | D | 50 | nd |
| pGfaCAT-46 | A | B | | 500 | 20 |
| pGfaCAT-29 | | B | D | 500 | 17 |
| pGfaCAT-28 | A | B | D | 1000 | 25 |

Figure 3A:
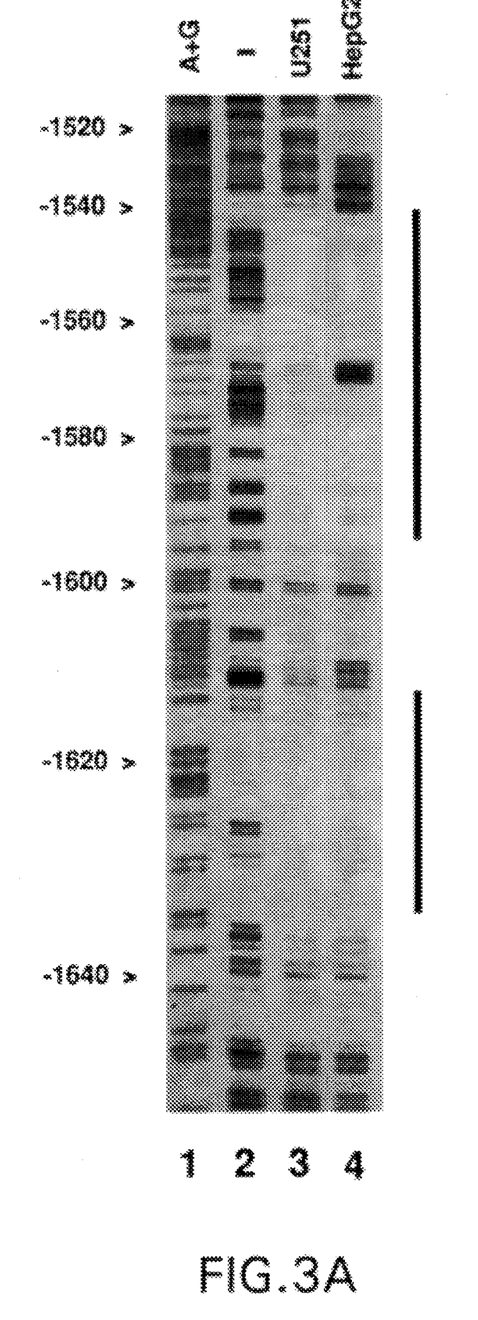
FIGS. 3A and 3B. Footprints of the gfa regulatory regions. Footprinting was conducted as described in Materials and Methods in the absence of nuclear extract (−) or with U251 or HepG2 nuclear extract as indicated.
Figure 3B:
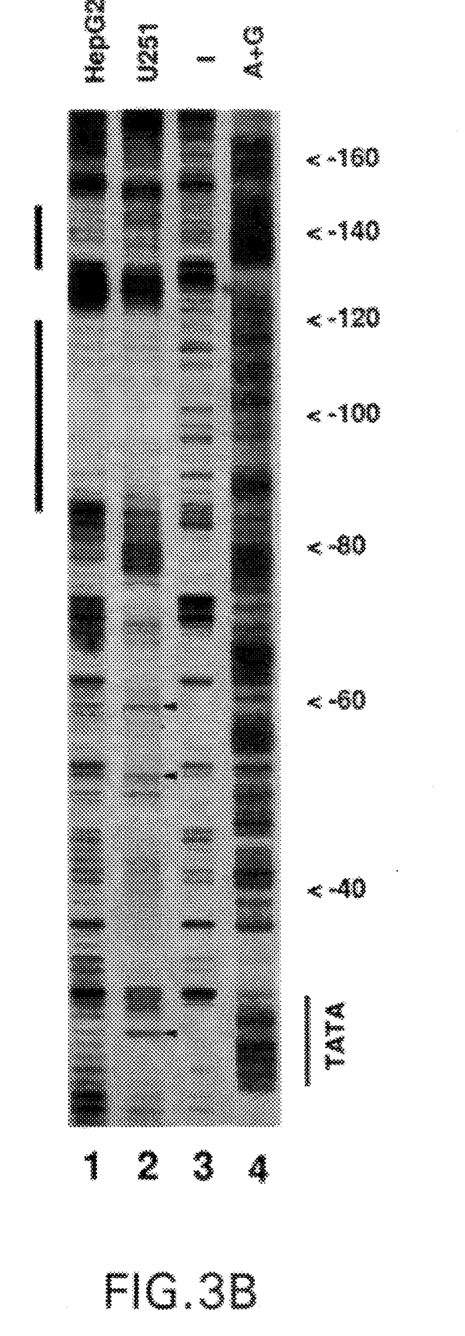

The indicated gfa upstream regions were joined to the gfa basal promoter. Region A extends from −1757 to −1604, B from −1612 to −1489, D from −132 132 to −57, and the basal promoter from −56 to +88. Values are expressed as a percentage of pGfaCAT-4 in U251 cells spans bp −1757 to −1604 and includes the first footprint, while region B spans bp −1612 to −1489 and includes the second footprint (FIG. 3A). The footprint-containing promoter proximal region in pGfaCAT-28, from bp −132 to −57, is labeled the D region (FIG. 3B). The contributions of these three regions to transcriptional activity were examined by transfecting U251 cells with reporter genes containing various combinations of these segments in front of the gfa basal promoter (bp −56 to +88) (Table 2). When tested individually, relatively little activity was supported by either the A or the D region, whereas the B region strongly stimulated CAT production. The activity observed for each paired combination was essentially the same as that produced by the stronger of the two regions alone, while the combination of all three segments resulted in a modest increase.

Cell specificity. Transfections of the two full-length constructs, pGfaCAT-2 and pGfaCAT-4, into various glial and nonglial cell lines showed that they carry the determinants for cell-specific expression (Table 1). Strong expression was obtained in primary astrocytes and the glial cell lines U251 and C6, while no significant activity was produced in the nonglial cell lines HepG2 and BHK. To determine if sequences responsible for this selectivity reside in the A, B, or D regions described above, the constructs containing one or more of these regions linked to the gfa basal promoter were tested (Table 2). As shown in the table, these plasmids produced little if any CAT activity in the nonglial HepG2 cells (compare to activity produced by the promoterless pSVoCAT plasmid, Table 1). Of particular note, the combination of the B region and the basal promoter (pGfaCAT-47) was almost inactive, although it produced high CAT levels in U251 cells. This indicates that the gfa sequences in this plasmid can determine cell specificity.

To determine if this specificity is reflected in different binding of proteins to the gfa regulatory regions, the DNaseI footprint pattern produced by U251 extracts was compared to that produced by extracts from the non-expressing HepG2 cells (FIGS. 3A and 3B). Although the two footprints were broadly similar, the HepG2 extract produced several qualitative differences in the pattern of DNaseI cleavage, as well as generally yielding weaker and less extensive protection. Particularly noticeable in the B region footprint (FIG. 3A, upper footprint) are two bands near position −1572 that were rendered hypersensitive by HepG2 extract but not by U251 extract. Other alterations in the cleavage pattern were present at the borders of both the B region and D region footprints (FIG. 3B, lower footprint). Particularly striking in the promoter proximal region are differences which persisted 3' of the major protected sequence in the D region. In this segment, the HepG2 extract produced a pattern of band intensities that closely matched that of the unprotected control, whereas the U251 extract produced an altered pattern. Since this altered pattern does not include an extended span of protected nucleotides, it might result from a change in DNA conformation produced by proteins binding elsewhere, rather than be due to direct binding to the site. However, in either event, it is further evidence for differential binding of U251 and HepG2 proteins.

All the gfa constructions discussed to this point contain the gfa basal promoter segment. Consequently, it is possible that sequences within this region participate in the tissue selectivity of gfa expression. This point was explored by making chimeric plasmids between gfa and SV40 elements; pGfaCAT-35 contains the A, B, and D regions of gfa in front of the SV40 early promoter, while pGfaCAT-22 contains the SV40 enhancer upstream of the gfa sequences of pGfaCAT-1, which includes the gfa D region and basal promoter (Table 3). In U251 cells, the gfa A, B, and D regions produced a 12-fold enhancement of activity from the SV40 early promoter (compare pGfaCAT-35 to pCAT-P), and the gfa promoter and D region supported even higher activation by the SV40 enhancer than did the SV40 early promoter (compare pGfaCAT-22 to pSV2CAT). These results show that both the gfa basal promoter and upstream regulatory regions can interact with heterologous transcription elements. In the nonglial HepG2 cells, the gfa promoter again was strongly activated by the SV40 enhancer, although not to the extent as in U251 cells. In contrast, the gfa A, B, and D regions failed to activate the SV40 promoter. These results suggest that these upstream regions of the gfa gene are primarily responsible for the control of its cell-specific transcription, although the basal promoter may also make a contribution (compare pGfaCAT-22 activity in U251 and HepG2 cells).

TABLE 3

Expression of gfa/SV40 chimeric plasmids

| Plasmid | Upstream Region | Promoter | CAT Activity U251 | CAT Activity HepG2 |
| --- | --- | --- | --- | --- |
| pSV0CAT | — | — | 30 | 42 |
| pGfaCAT-1 | D | gfa | 10 | 7 |
| pGfaCAT-28 | A + B + D | gfa | 1000 | 25 |
| pGfaCAT-22 | SV40 + D | gfa | 18600 | 3200 |
| pGfaCAT-35 | A + B + D | SV40 | 9600 | 240 |
| pSV2CAT | SV40 | SV40 | 8250 | 8250 |
| pCAT-P | — | SV40 | 750 | 240 |

Upstream and promoter regions were combined as indicated. Values are expressed as a percentage of pGfaCAT-4 in U251 cells.

Preparation of Transgenic Animals

Following procedures well known in the art, as exemplified by Mucke et al. (36) and Leder et al. (40), one of ordinary skill in the art can prepare transgenic mammals (e.g., mice) by injecting the disclosed gfa gene constructs (e.g., plasmid pGfa CAT-22) into the germline of the mammal or into the male pronuclei of fertilized one-cell mouse eggs which are subsequently transferred to pseudo-pregnant foster females. Via these procedures, transgenic animals having the gfa gene construct capable of expressing exogenous or endogenous protein in the astrocytes, can be produced. More particularly, where the gfa gene construct encodes the amyloid protein, a transgenic animal model mimicking Alzheimer's disease can be produced.

Based on the foregoing, the ordinary skilled artisan can express many different kinds of proteins in astrocytes, including:

1. Hormones, growth factors, and their receptors. Examples include basic fibroblast growth factor (bFGF), acidic FGF (aFGF), platelet derived growth factor (PDGF), insulin like growth factors 1 and 2 (IGF-1, IGF-2), epidermal growth factor (EGF), transforming growth factors $\beta$-1 and $\beta$-2 (TGF$\beta$1, TGF$\beta$2), and S100$\beta$.

2. Proteins encoded by oncogenes like myc, fos, and erb-a.

3. Ion channels like the calcium channel and the potassium channel.

4. Metabolic enzymes, especially ones involved in processing drugs or neurotransmitters; e.g., glutamine synthetase.

Additionally, in each case, a dominant dysfunctional protein, an antisense RNA, or a ribozyme, all of which can inhibit the function or production of the protein, can also be expressed.

In the present invention, transient transfection of CAT reporter plasmids was used to identify segments of the gfa gene that regulate its expression. In order to obtain significant CAT activity in these experiments, two changes were made in the standard transfection protocol. First, constructs contained a region downstream of the RNA startpoint that included part of the gfa coding region and, second, cells were transfected 4 days after plating. The downstream region was included in the plasmids because in vitro studies had indicated it was required for efficient gfa transcription (6). The inventors subsequently confirmed this result in vivo, finding that deletion of bp +9 to +38 from pGfacat-4 severely reduced its activity (7).

The need to transfect cells at high density for strong pGfaCAT-2 expression mirrors activation of the endogenous gfa gene. The levels of both endogenous gfa mRNA and GFAP protein increase with cell density, indicating that the density-dependent regulation is due to either enhanced mRNA synthesis or stability. If the mechanism is differential stability, then the critical RNA sequence must reside in the first 47 nucleotides, as only this segment is shared by the endogenous gfamRNA and the gfa-CATRNA fusion encoded by pGfaCAT-2. Regulation at the transcription level could be mediated by cell density-dependent changes in the kind or quantity of a specific transcription factor. Since pGfaCAT-2 is responsive to the cell density signal, it should be possible to analyze the mechanism of this regulation using methods similar to those used here to investigate cell-specific regulation.

The transfection studies and footprint analyses identified three regions, A, B, and D, which when combined with the gfa basal promoter are both necessary and sufficient for efficient expression. Of these three regions, B is clearly the most effective in activating transcription (Table 2). When joined directly to the basal promoter, B (pGfaCAT-47) supports strong CAT activity, while A (pGfaCAT-65) and D (pGfaCAT-1) produce very little. Furthermore, addition of either A or D to B does not increase expression (pGfaCAT-46 and −29, respectively), while adding both (pGfaCAT-28) produces a modest increase. It was surprising to find that while D is crucial when B is near its natural position (compare pGfaCAT-4 and −16, FIG. 2), it is superfluous when B is artificially positioned near the promoter (compare pGfaCAT-29 and −47, Table 2). A possible explanation is that a primary function of D is to position B close to the basal promoter. A corollary of this model is that the activity of the gfa gene could be regulated by factors that influence the positioning of the B segment, without any requirement that such factors interact directly with the basal transcription machinery.

When joined with the gfa basal promoter, the B region alone or in combination with A and D activates transcription in a cell-specific manner, expression being far stronger in the glial cell lines than in the nonglial cells (Tables 1 and 2). Studies in which the gfa upstream region or basal promoter was interchanged with its SV40 complement found that both regions responded to their SV40 complements in U251 cells, but whereas the gfa promoter remained active in HepG2 cells, the A, B, and D regions did not (Table 3). These results indicate that control of cell specificity resides primarily in the upstream A, B, and D regions. Consistent with these observations is the finding that the DNaseI footprints produced in these regions by a nuclear extract from U251 cells differed from that produced by an extract from HepG2 cells.

Figure 4:
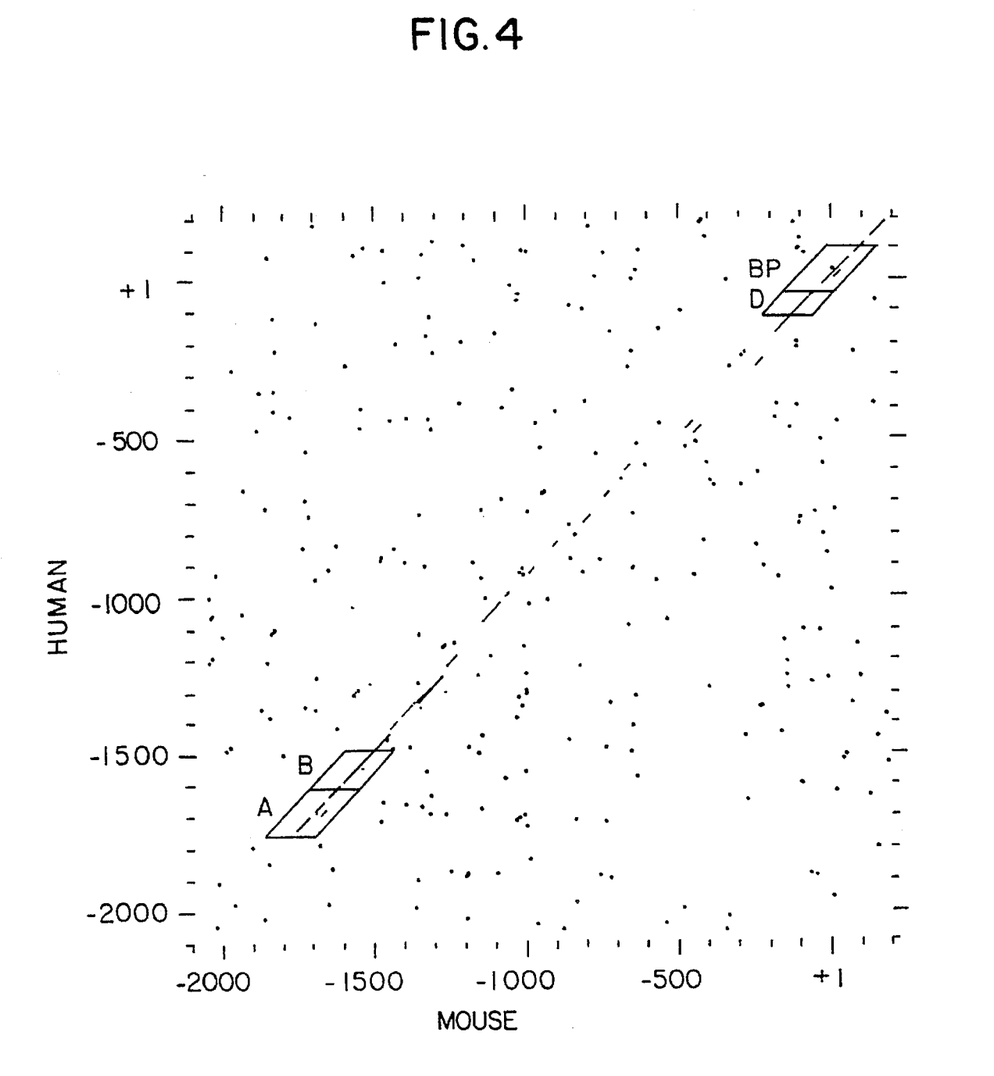
FIG. 4. Sequence comparison of the 5' regions of the human and mouse gfa genes.

While the experiments described herein were being performed, Miura et al. (21) published an analysis of transcription of the mouse gfa gene in which 2500 bp of 5'-flanking DNA were examined for regions regulating its transcription. In contrast to the results reported here, the workers found the segment homologous to the present A and B regions to produce only a marginal, 1.5-fold stimulation of transcription, significant activation being produced solely by a promoter-proximal segment homologous to the D region. The present inventors have compared the 5' regions of the human and mouse gfa genes. Sequences extending from −2100 to +200 of each gene were compared by the University of Wisconsin Genetics Computer Group Compare Program, using the default values for window and stringency (21 and 14, respectively). Isolated regions of homology are indicated by dots; in extended regions of homology, the dots merge to form a line. The regions corresponding to the human A, B, D and basal promoter (BP) segments are indicated. The human sequence is from this work, the mouse sequence is from (21).

Figure 5:
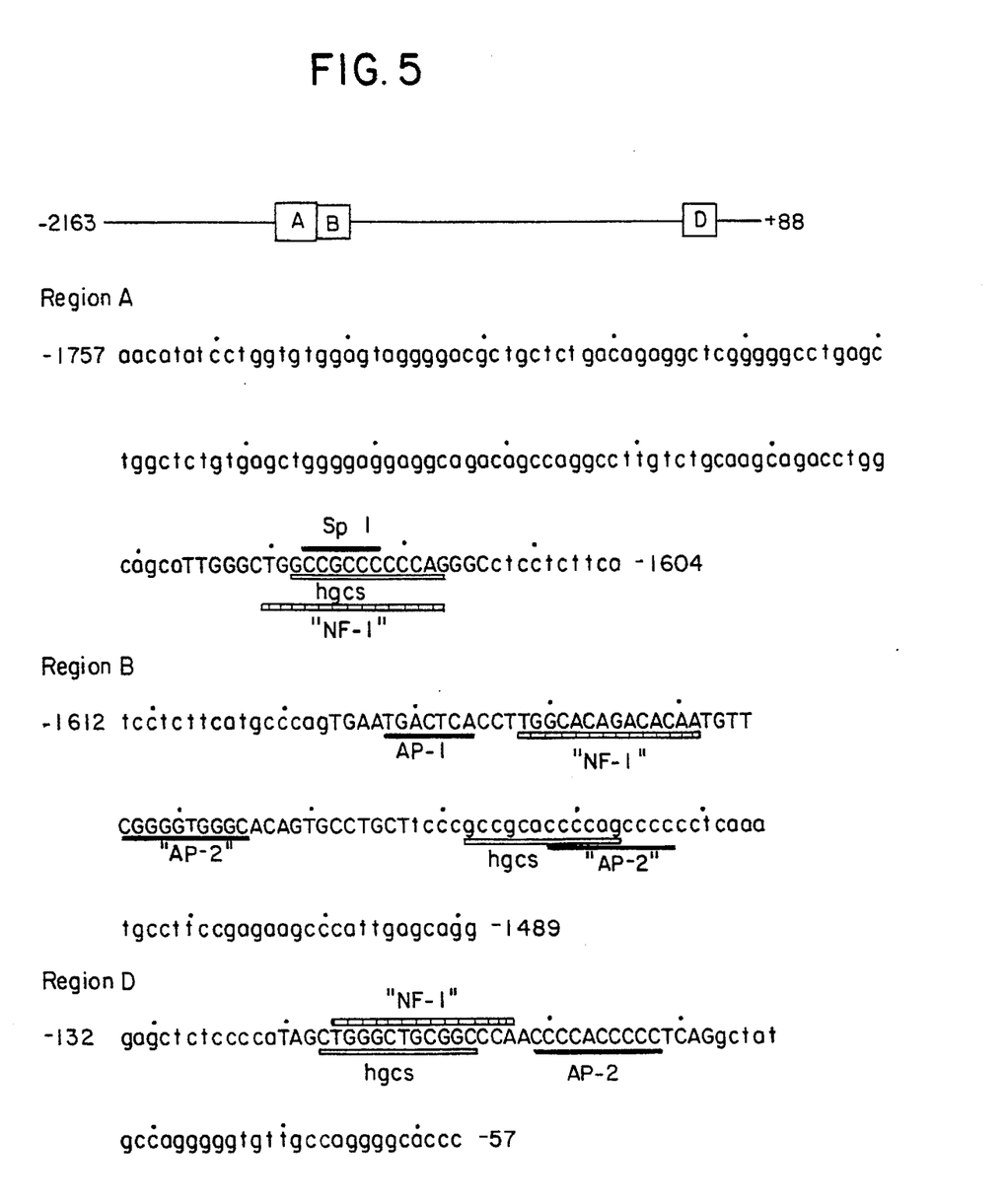
FIG. 5. Sequences of the gfa regulatory regions, SEQ ID NO:1, SEQ ID NO:2 and SEQ ID NO:3.

The primary long-term goal of the present invention is to identify and characterize astrocyte-specific transcription factors. However, previously identified factors may also participate in astrocyte-specific transcription; for example, the fairly ubiquitous Sp 1 and serum-response factor proteins are required for functioning of the muscle-specific transcription factor Myo D1 (23). Potential binding sites for known factors in the gfa A, B and D regions include those for Sp 1 (CCGCCC) (24), AP-1 (TGACTCA) (25, 26), and AP-2 (CCCCACCCCC) (Seq. ID No. 4) (27, 28) In FIG. 5, the sequences of the gfa A, B, and D regulatory regions are presented, with upper case letters indicating the footprinted segments and positions of potential regulatory sites shown. Quotation marks around the AP-2 designations in the B region and the NF-1 designations indicate that these sequences differ somewhat from the documented binding sites of CCCCACCCCC (Seq. ID No. 4) (27, 28) and TGGA/CN5GCCAA (Seq. ID No. 7) (31), respectively. The position of each region within the gfa segment of pGfaCAT-4 is shown at the top. In addition, a possible CRE site (TGACCTCA) lies just upstream of the D region between −152 and −145; its sequence differing only at the underlined base from the consensus CRE, TGACGTCA (28). A novel sequence of interest is the 12 base motif GCCGCNNCCCAG (Seq. ID No. 5), exact copies of which are found in each of the A, B and D regions (FIG. 5). This segment, which we will refer to as the human gfa common sequence (hgcs), is located within the footprints of the A and D regions (the sequence is the reverse complement in D), and is just 3' of the footprint in the B region, but is not otherwise found in the gfa 5' region we have used here. The hgcs in D also overlaps a nearly perfect 14 bp inverted repeat (bp −116 to −103).

5'-Flanking sequences have been reported for two other genes expressed predominantly in glial cells, the JC virus (JCV) (30) and human S100β (29). The critical regions for JCV expression are two 92-bp repeats (30), while those for S100β have not yet been ascertained. Comparison of the JCV 92 bp repeat to the gfa A, B, and D regions showed no strong homologies, although sequences related to its NF-1 binding site (32, 33) are present within each of the footprinted regions (FIG. 5). Like gfa, the S100β 5'-flanking region contains a putative AP-2 site (CCCCACCCCC (Seq. ID No. 4), at bp −308) and CRE site (TGACATCA, at bp −282). Strikingly, a repeated motif previously recognized in the S100β promoter region (29) is related to the hgcs. The two closest matches, GCCcCNNCCCAc (Seq. ID No. 6) and cCCtCNNCCCAG (Seq. ID No. 6) (lower case letters indicate deviating nucleotides), are present as inverted repeats flanking the putative TATA box. The function of these latter sequences is unknown.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

LITERATURE CITED

1. Kimelberg, H. K., and Norenberg, M. D. (1989) Sci. Am. 260, 66–76.
2. Norenberg, M. D., Hertz, L., and Schousboe, A. eds. (1988) The Biochemical Pathology of Astrocytes. Alan R. Liss, Inc., New York.
3. Eng, L. F. (1980) in Proteins of the Nervous System, 2nd Ed., (Bradshaw, R. A., and Schneider, D. M. eds.), pp. 85–117, Raven Press, New York.
4. Chiu, F. C., and Goldman, J. E. (1985) J. Neuroimmunol. 8, 283–292.
5. Brenner, M., Lampel, K., Nakatani, Y., Mill, J., Banner, C., Mearow, K., Dohadwala, M., Lipsky, R., and Freese, E. (1990) Mol. Brain Res. 7, 277–286.
6. Nakatani, Y., Brenner, M., and Freese, E. (1990) Proc. Natl. Acad. Sci. USA 87, 4289–4293.
7. Nakatani, Y., Horikoshi, M., Brenner, M., Yamamoto, T., Besnard, F., Roeder, R. G., and Freese, E. (1990) Nature 348, 86–88.
8. Ausubel, F. M., Brent, R., Kingston, R. E., Moore, D. D., Seidman, J. G., Smith, J. A., and Struhl, K. (1988) Current Protocols in Molecular Biology. Wiley, N.Y.
9. Clewell, D. B., and Helinski, D. R. (1969) Proc. Natl. Acad. Sci. USA 62, 1159–1166.
10. Nordeen, S. K. (1988) Biotechniques 6, 454–457.
11. Gorman, C. M., Moffat, L. F., and Howard, B. H. (1982) Mol. Cell. Biol. 2, 1044–1051.
12. Magnuson, M. A., Quinn, P. G., and Granner, D. K. (1987) J. Biol. Chem. 262, 14971–14920.
13. Kunkel, T. A., Roberts, J. D., and Zakour, R. A. (1987) Methods Enzymol. 154, 367–382.
14. Pfreundschuh, M., Shiku, H., Takashai, T., Ueda, R., Ransohoff, J., Oettgen, H. F., and Old, L. J. (1978) Proc. Natl. Acad. Sci. USA 75, 5122–5126.
15. Besnard, F., Perraud, F., Sensenbrenner, M., and Labourdette, G. (1987) Neurosci. Lett. 73, 287–292.
16. de Wet, J. R., Wood, K. V., DeLuca, M., Helinski, D. R., and Subramani, S. (1987) Mol. Cell. Biol. 7, 725–732.
17. Besnard, F., Perraud, F., Sensenbrenner, M., and Labourdette, G. (1989) Int. J. Dev. Neurosci. 7, 401–409.
18. Dignam, J. D., Martin, P. L., Shastry, B. S., and Roeder, R. G. (1983) Methods Enzymol. 101, 582–598.
19. Jones, K. A., Yamamoto, K. R., and Tjian, R. 1985. Cell 42, 559–572.
20. Raju, T. R., Bignami, A., and Dahl, D. (1980) Brain Res. 200, 225–230.
21. Miura, M., Tamura, T., ande Mikoshiba, K. (1990) J. Neurochem. 55, 1180–1188.
22. Schmid, C. W., and Jelinek, W. R. (1982) Science 216, 1065–1070.
23. Sartorelli, V., Webster, K., and Kedes, L. (1990) Genes Dev. 4, 1811–1822.
24. Kadonaga, J. T., Jones, K. A., and Tjian, R. (1986) Trends Biol. Sci. 11, 20–23.
25. Angel, P., Imagawa, M., Chiu, R., Stein, B., Imbra, R. J., Rahmsdorf, H. J., Jonat, C., Herrlich, P., and Karin, M. (1987) Cell 49, 729–739.
26. Lee, W., Mitchell, P., and Tjian, R. (1987) Cell 49, 741–752.
27. Medcalf, R. L., Ruegg, M., and Schleuning, W. D. (1990) J. Biol. Chem. 265, 14618–14626.
28. Roesler, W. J., Vandenbark, G. R., and Hanson, R. W. (1988) J. Biol. Chem. 263, 9063–9066.
29. Allore, R. J., Friend, W. C., O'Hanlon, D., Neilson, K. M., Baumal, R., Dunn, R. J., and Marks, A. (1990) J. Biol. Chem. 265, 15537–15543.
30. Frisque, R. J., Bream, G. L., and Cannella, M. T. (1984) J. Virol. 51, 458–469.
31. Gronostajski, R. M. (1987) Nucleic Acids Res. 15, 5545–5559.
32. Amemiya, K., Traub R., Durham, L., and Major, E. O. (1989) J. Biol. Chem. 264, 7025–7032.
33. Tamura, T. A., Inoue, T., Nagata, K., and Mikoshiba, K. (1988) Biochem. Biophys. Res. Comm. 157, 419–425.
34. Sensenbrenner, M., Devilliers, G., Bock, E., and Porte, A. (1980) Differentiation 17, 51–61.
35. Shafit-Zagardo, B., Kume-Iwaki, A., and Goldman, J. E. (1988) Glia 1, 346–354.
36. Mucke, Lennart, Oldstone, Michael, B. A., Morris, James C., and Nirenberg, Michael I. (1991). The New Biologist 3, 465–474.
37. Wirak, Dana O., Bayheys, Richard, Kundel, Catherine A., Trapp, Bruce D., and Unterbeck, Alex J. (1991). EMBO Journal 10, 289–296.
38. Sarid, J. (1991). Journal of Neuroscience. Res. 28, 217–228.
39. Sakar, Srijata, Cowan, Nicholas (1991). Journal of Neurochemistry 57 675–684.
40. Leder, Philip, Stewart, Timothy A. U.S. Pat. No. 4,736,866 (1986).

---

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 154 base pairs
( B ) TYPE: nucleic acid
( C ) STRANDEDNESS: double ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( v i i ) IMMEDIATE SOURCE:
    ( A ) LIBRARY: Fetal Liver Charon 4A (ATCC 3733)

( i x ) FEATURE:
    ( A ) NAME/KEY: enhancer
    ( B ) LOCATION: 1..154
    ( D ) OTHER INFORMATION: /standard_name= "GFAP enhancer"
        / label= enhancer ( i x ) FEATURE:
    ( A ) NAME/KEY: protein_bind
    ( B ) LOCATION: 127..141
    ( D ) OTHER INFORMATION: /function= "transcription enhancer"
        / bound_moiety= "NF-1"
        / standard_name= "NF-1 like"

( i x ) FEATURE:
    ( A ) NAME/KEY: protein_bind
    ( B ) LOCATION: 130..135
    ( D ) OTHER INFORMATION: /function= "transcription enhancer"
        / bound_moiety= "Sp1"
        / standard_name= "Sp1 site"

( i x ) FEATURE:
    ( A ) NAME/KEY: repeat_unit
    ( B ) LOCATION: 129..141
    ( D ) OTHER INFORMATION: /function= "unknown"
        / rpt_type= "direct"
        / rpt_family= "hgcs"
        / label= repeat_unit ( x i ) SEQUENCE DESCRIPTION: SEQ ID NO:1:

```
AACATATCCT GGTGTGGAGT AGGGGACGCT GCTCTGACAG AGGCTCGGGG GCCTGAGCTG      60
GCTCTGTGAG CTGGGGAGGA GGCAGACAGC CAGGCCTTGT CTGCAAGCAG ACCTGGCAGC     120
ATTGGGCTGG CCGCCCCCCA GGGCTCCTC TTCA                                  154
```

( 2 ) INFORMATION FOR SEQ ID NO:2:

( i ) SEQUENCE CHARACTERISTICS:
        ( A ) LENGTH: 124 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( v i i ) IMMEDIATE SOURCE:
    ( A ) LIBRARY: Fetal Liver Charon 4A (ATCC 3733)

( i x ) FEATURE:
    ( A ) NAME/KEY: enhancer
    ( B ) LOCATION: 1..124
    ( D ) OTHER INFORMATION: /standard_name= "GFAP enhancer"
        / label= enhancer ( i x ) FEATURE:
    ( A ) NAME/KEY: protein_bind
    ( B ) LOCATION: 21..27

(D) OTHER INFORMATION: /function= "transcription enhancer"
/ bound_moiety= "AP-1"
/ standard_name= "GFAP enhancer"
/ label= protein_bind (ix) FEATURE:
(A) NAME/KEY: protein_bind
(B) LOCATION: 48..58
(D) OTHER INFORMATION: /function= "transcription enhancer"
/ bound_moiety= "AP-2"
/ standard_name= "AP-2-like site"

(ix) FEATURE:
(A) NAME/KEY: protein_bind
(B) LOCATION: 31..44
(D) OTHER INFORMATION: /function= "transcription enhancer"
/ bound_moiety= "NF-1"
/ standard_name= "NF-1-like site"

(ix) FEATURE:
(A) NAME/KEY: protein_bind
(B) LOCATION: 81..91
(D) OTHER INFORMATION: /function= "transcription enhancer"
/ bound_moiety= "AP-2"
/ standard_name= "AP-2-like site"

(ix) FEATURE:
(A) NAME/KEY: repeat_unit
(B) LOCATION: 75..86
(D) OTHER INFORMATION: /function= "unknown"
/ rpt_type= "direct"
/ rpt_family= "hgcs"
/ label= repeat_unit (xi) SEQUENCE DESCRIPTION: SEQ ID NO:2:

```
TCCTCTTCAT GCCCAGTGAA TGACTCACCT TGGCACAGAC ACAATGTTCG GGGTGGGCAC      60
AGTGCCTGCT TCCCGCCGCA CCCCAGCCCC CCTCAAATGC CTTCCGAGAA GCCCATTGAG     120
CAGG                                                                  124
```

(2) INFORMATION FOR SEQ ID NO:3:

(i) SEQUENCE CHARACTERISTICS:
(A) LENGTH: 76 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (vii) IMMEDIATE SOURCE:
(A) LIBRARY: Fetal Liver Charon 4A (ATCC 3733)

(ix) FEATURE:
(A) NAME/KEY: enhancer
(B) LOCATION: 1..76
(D) OTHER INFORMATION: /standard_name= "GFAP enhancer"
/ label= enhancer (ix) FEATURE:
(A) NAME/KEY: protein_bind
(B) LOCATION: 17..30
(D) OTHER INFORMATION: /function= "transcription enhancer"
/ bound_moiety= "NF-1"
/ standard_name= "NF-1 like site"

(ix) FEATURE:
(A) NAME/KEY: protein_bind
(B) LOCATION: 42..52
(D) OTHER INFORMATION: /function= "transcription enhancer"

/ bound_moiety= "AP-2"
/ standard_name= "AP-2 site"

( i x ) FEATURE:
    ( A ) NAME/KEY: repeat_unit
    ( B ) LOCATION: 16..27
    ( D ) OTHER INFORMATION: /function= "unknown"
        / rpt_type= "inverted"
        / rpt_family= "hgcs"
        / label= repeat_unit ( x i ) SEQUENCE DESCRIPTION: SEQ ID NO:3:

```
GAGCTCTCCC   CATAGCTGGG   CTGCGGCCCA   ACCCCACCCC   CTCAGGCTAT   GCCAGGGGGT          60
GTTGCCAGGG   GCACCC                                                                 76
```

( 2 ) INFORMATION FOR SEQ ID NO:4:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear     ( i i ) MOLECULE TYPE: DNA (genomic)

( i x ) FEATURE:
        ( A ) NAME/KEY: protein_bind
        ( B ) LOCATION: 1..10
        ( D ) OTHER INFORMATION: /function= "transcription enhancer"
            / bound_moiety= "AP-2"
            / standard_name= "AP-2 site"

( x i ) SEQUENCE DESCRIPTION: SEQ ID NO:4:

```
CCCCACCCCC                                                                          10
```

( 2 ) INFORMATION FOR SEQ ID NO:5:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear     ( i i ) MOLECULE TYPE: DNA (genomic)

( i x ) FEATURE:
        ( A ) NAME/KEY: repeat_unit
        ( B ) LOCATION: 1..12
        ( D ) OTHER INFORMATION: /function= "unknown"
            / rpt_type= "direct"
            / rpt_family= "hgcs"
            / standard_name= "hgcs sequence"
            / label= repeat_unit ( x i ) SEQUENCE DESCRIPTION: SEQ ID NO:5:

```
GCCGCNNCCC   AG                                                                     12
```

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear     ( i i ) MOLECULE TYPE: DNA (genomic)

(ix) FEATURE:
    (A) NAME/KEY: repeat_unit
    (B) LOCATION: 1..12
    (D) OTHER INFORMATION: /function= "unknown"
        / rpt_type= "inverted"
        / rpt_family= "S100B promoter"
        / label= repeat_unit (xi) SEQUENCE DESCRIPTION: SEQ ID NO:6:

S C C Y C N N C C C A S                                           12

(2) INFORMATION FOR SEQ ID NO:7:

(i) SEQUENCE CHARACTERISTICS:
        (A) LENGTH: 14 base pairs
        (B) TYPE: nucleic acid
        (C) STRANDEDNESS: double
        (D) TOPOLOGY: linear     (ii) MOLECULE TYPE: DNA (genomic)

(ix) FEATURE:
        (A) NAME/KEY: protein_bind
        (B) LOCATION: 1..14
        (D) OTHER INFORMATION: /function= "transcription enhancer"
            / bound_moiety= "NF-1"
            / standard_name= "NF-1-like site"

(xi) SEQUENCE DESCRIPTION: SEQ ID NO:7:

T G G M N N N N G C C A A                                          14

What is claimed is:

1. A recombinant DNA molecule comprising a nucleotide sequence from nucleotide position −2163 to nucleotide position +88 of a human gene encoding glial fibrillary acidic protein, where +1 is the RNA start site, operably linked to a heterologous gene.

2. A recombinant DNA molecule comprising the following operatively linked elements:
    (a) a control region selected from the group consisting of
        (i) the SV40 enhancer ligated to nucleotides having the sequence of SEQ. I.D. NO. 3, and
        (ii) nucleotides −1757 to −1489 ligated to nucleotides −132 to −57, where the nucleotide ranges refer to the human gene for glial fibrillary acidic protein and where +1 is the RNA start site;
    (b) a basal promoter; and
    (c) a heterologous gene;
wherein said elements are ordered 5'-(a)-(b)-(c)-3'.

3. A recombinant DNA molecule comprising the following operatively linked elements ordered 5' to 3': a DNA molecule having the nucleotide sequence of SEQ. I.D. NO. 2, a basal promoter being a basal promoter of a human gfa gene, and a heterologous gene.

4. An isolated human astrocyte-specific DNA expression vector comprising the following elements operably linked in 5' to 3' order: a control region, a basal promoter being a basal promoter of a human gfa gene, and a heterologous gene wherein the control region is selected from the group consisting of     nucleotides −1757 to −1489 ligated to nucleotides −132 to −57,     nucleotides −1757 to −1489,     nucleotides −1612 to −1489, and     nucleotides −1612 to −57;

where the nucleotide ranges refer to a human gene encoding glial fibrillary acidic protein and where +1 is the RNA start site.

5. A recombinant DNA molecule comprising three control regions, wherein two of said control regions have the nucleotide sequence GCCGCNNCCCAG (SEQ ID NO:5) and the third of said control regions has the nucleotide sequence CTGGGNNGCGGC (reverse complement of SEQ ID NO:5), wherein all of said control regions are operatively linked to a basal promoter and a heterologous gene, at a position upstream of said basal promoter, such that the transcription of said heterologous gene is increased compared to the transcription of said heterologous gene in the absence of said nucleotide sequences when said recombinant DNA molecule is expressed in a host cell.

6. An isolated human astrocyte-specific DNA expression vector comprising the following elements operably linked in 5' to 3' order: a control region, a basal promoter being a basal promoter of a human gfa gene, and a heterologous gene wherein the control region is selected from the group consisting of     a nucleotide sequence comprising nucleotides −1757 to −1489 and nucleotides −132 to −57, where said nucleotides −1757 to −1489 are positioned 5' to nucleotides −132 to −57,     nucleotides −1757 to −1489,     nucleotides −1612 to −1489, and     nucleotides −1612 to −57;

where the nucleotide ranges refer to a human gene encoding glial fibrillary acidic protein and where +1 is the RNA start site.

7. A recombinant DNA molecule comprising the following operatively linked elements:
    (a) a control region selected from the group consisting of
        (i) a nucleotide sequence comprising the SV40 enhancer and nucleotides having the sequence of SEQ. I.D. NO. 3, where said SV40 enhancer is positioned 5' to the nucleotides having the sequence of SEQ. I.D. NO. 3, (ii) a nucleotide sequence comprising nucleotides −1757 to −1489 and nucleotides −132 to −57, where the nucleotide ranges refer to the human gene for glial fibrillary acidic protein and where +1 is the RNA start site and where said nucleotides −1757 to −1489 are positioned 5' to said nucleotides −132 to −57;

(b) a basal promoter; and (c) a heterologous gene;

wherein said elements are ordered 5'-(a)-(b)-(c)-3'.

8. An isolated human astrocyte-specific DNA expression vector comprising the following elements operably linked in 5' to 3' order: at least one control region, a basal promoter being a basal promoter of a human gfa gene, and a heterologous gene wherein the control regions are selected from the group consisting of nucleotides −1757 to −1489 ligated to nucleotides −132 to −57, nucleotides −1757 to −1489, nucleotides −1612 to −1489, and nucleotides −1612 to −57;

where the nucleotide ranges refer to a human gene encoding glial fibrillary acidic protein and where +1 is the RNA start site.

9. An isolated human astrocyte-specific DNA expression vector comprising the following elements operably linked in 5' to 3' order: at least one control region, a basal promoter, and a heterologous gene wherein the control regions are selected from the group consisting of a nucleotide sequence comprising of nucleotides −1757 to −1489 and nucleotides −132 to −57, wherein said nucleotides −1757 to −1489 are positioned 5' to nucleotides −132 to −57, nucleotides −1757 to −1489, nucleotides −1612 to −1489, and nucleotides −1612 to −57;

where the nucleotide ranges refer to a human gene encoding glial fibrillary acidic protein and where +1 is the RNA start site.

10. A plasmid containing the recombinant DNA molecule of claim 1, wherein said recombinant DNA molecule is operably linked to additional transcription control sequences.

11. A plasmid containing the recombinant DNA molecule of claim 1, wherein said recombinant DNA molecule is operably linked to additional transcription control sequences.

12. A plasmid containing the DNA expression vector of claim 6, wherein said DNA expression vector is operably linked to additional transcription control sequences.

13. A plasmid according to claim 9, selected from the group consisting of pGfa CAT-28, pGfa CAT-29, pGfa CAT-35, pGfa CAT-46, and pGfa CAT-47.

14. A plasmid containing the recombinant DNA molecule of claim 7, wherein said recombinant DNA molecule is operably linked to additional transcription control sequences.

15. A plasmid containing the DNA expression vector of claim 8, wherein said DNA expression vector is operably linked to additional transcription control sequences.

16. A plasmid containing the DNA expression vector of claim 9, wherein said DNA expression vector is operably linked to additional transcription control sequences.

17. A mammalian glial cell line comprising cells transfected with the recombinant DNA molecule of claim 5.

18. A mammalian glial cell line comprising cells transfected with the expression vector of claim 6.

19. A mammalian glial cell line comprising cells transfected with the recombinant DNA molecule of claim 7.

20. A mammalian glial cell line comprising cells transfected with the expression vector of claim 8.

21. A mammalian glial cell line comprising cells transfected with the expression vector of claim 9.

22. The mammalian glial cell line of claim 17, wherein said cells are astrocyte cells.

23. The mammalian glial cell line of claim 18, wherein said cells are astrocyte cells.

24. The mammalian glial cell line of claim 21, wherein said cells are astrocyte cells.

25. The mammalian glial cell line of claim 17, wherein said cells are U251 cells.

26. The mammalian glial cell line of claim 21, wherein said cells are U251 cells.

27. The mammalian glial cell line of claim 17, wherein said heterologous gene encodes human amyloid protein.

28. A method for expressing a protein comprising transfecting a mammalian glial cell line with the recombinant DNA molecule of claim 1 and culturing said cell line under conditions suitable to express said protein.

29. A method for expressing a protein comprising transfecting a mammalian glial cell line with the recombinant DNA molecule of claim 3 and culturing said cell line under conditions suitable to express said protein.

30. A method for expressing a protein comprising transfecting a mammalian glial cell line with the expression vector of claim 6 and culturing said cell line under conditions suitable to express said protein.

31. A method for expressing a protein comprising transfecting a mammalian glial cell line with the recombinant DNA molecule of claim 7 and culturing said cell line under conditions suitable to express said protein.

32. A method for expressing a protein comprising transfecting a mammalian glial cell line with the expression vector of claim 9 and culturing said cell line under conditions suitable to express said protein.

33. A recombinant DNA molecule as in claim 2, wherein said basal promoter is a basal promoter of a human gfa gene or an SV40 promoter.

34. A recombinant DNA molecule as in claim 6, wherein said basal promoter is a basal promoter of a human gfa gene or an SV40 promoter.

35. A plasmid according to claim 14, wherein said additional control sequences include an AP-1 site.

36. A plasmid according to claim 15, wherein said additional control sequences include an AP-1 site.

37. A plasmid according to claim 16, wherein said additional control sequences include an AP-1 site.

* * * * *